United States Patent
Tanaka et al.

(10) Patent No.: US 9,623,511 B2
(45) Date of Patent: Apr. 18, 2017

(54) CHIP FOR PLASMA GENERATION, PLASMA GENERATOR, AND PLASMA SPECTROMETRY METHOD

(71) Applicant: ARKRAY, Inc., Kyoto (JP)

(72) Inventors: Takashige Tanaka, Kyoto (JP); Yasunori Shiraki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 150 days.

(21) Appl. No.: 14/632,064

(22) Filed: Feb. 26, 2015

(65) Prior Publication Data

US 2015/0246410 A1 Sep. 3, 2015

(30) Foreign Application Priority Data

Feb. 28, 2014 (JP) .................. 2014-039507
Feb. 24, 2015 (JP) .................. 2015-033826

(51) Int. Cl.
*G01J 3/30* (2006.01)
*B23K 10/00* (2006.01)
(Continued)

(52) U.S. Cl.
CPC ............ *B23K 10/006* (2013.01); *G01J 3/12* (2013.01); *G01J 3/443* (2013.01); *G01N 21/67* (2013.01);
(Continued)

(58) Field of Classification Search
CPC . B23K 10/006; G01J 3/443; G01N 2021/054; G01N 21/67–21/69; H05H 1/46; H05H 1/48
See application file for complete search history.

(56) References Cited

U.S. PATENT DOCUMENTS 4,565,446 A * 1/1986 Chu .................. G01N 21/03
356/246
4,589,000 A * 5/1986 Koto .................. B41J 2/16544
347/30
(Continued)

FOREIGN PATENT DOCUMENTS

EP 1734360 A1 12/2006
EP 1 855 114 A1 11/2007
(Continued)

OTHER PUBLICATIONS

Extended European Search Report issued in corresponding European Patent Application No. 15157032.2 dated Oct. 30, 2015.
(Continued)

*Primary Examiner* — Kara E Geisel
*Assistant Examiner* — Rufus Phillips
(74) *Attorney, Agent, or Firm* — Morgan, Lewis & Bockius LLP

(57) ABSTRACT

A chip for plasma generation, a plasma generator, and a plasma spectrometry method, having high reproducibility of plasma light emission are described, wherein the chip for plasma generation contains a channel, wherein the channel has a first region, a narrow portion, and a second region, wherein the narrow portion is in communication with the first region and the second region and has a cross-sectional area smaller than the first region and the second region, and the chip further includes an air bubble movement prevention unit that prevents air bubbles generated in the narrow portion from moving from the narrow portion toward the upstream side of the narrow portion.

9 Claims, 4 Drawing Sheets

(51) Int. Cl.
*G01J 3/443* (2006.01)
*G01J 3/12* (2006.01)
*H05H 1/46* (2006.01)
*G01N 21/67* (2006.01)
*H05H 1/48* (2006.01)
*G01N 21/69* (2006.01)
*G01N 21/05* (2006.01)

(52) U.S. Cl.
CPC .............. *H05H 1/46* (2013.01); *H05H 1/48* (2013.01); *G01N 21/69* (2013.01); *G01N 2021/054* (2013.01)

(56) References Cited

U.S. PATENT DOCUMENTS

| | | | | |
|---|---|---|---|---|
| 5,264,130 | A * | 11/1993 | Etlin | C02F 1/006 210/195.3 |
| 5,932,100 | A * | 8/1999 | Yager | B01D 11/0492 210/511 |
| 7,875,825 | B2 | 1/2011 | Takamura et al. | |
| 7,948,619 | B2 * | 5/2011 | Huemer | B01L 3/502 356/246 |
| 2002/0045272 | A1 * | 4/2002 | McDevitt | B01L 3/0289 436/518 |
| 2007/0098232 | A1 | 5/2007 | Matula et al. | |
| 2007/0164003 | A1 | 7/2007 | Takamura et al. | |
| 2011/0201099 | A1 * | 8/2011 | Anderson | G01N 21/05 435/287.2 |
| 2013/0162736 | A1 * | 6/2013 | Paschkewitz | B41J 2/19 347/92 |
| 2013/0321803 | A1 | 12/2013 | Kohara et al. | |
| 2015/0015880 | A1 | 1/2015 | Kohara et al. | |

FOREIGN PATENT DOCUMENTS

| | | |
|---|---|---|
| EP | 2 002 883 A2 | 12/2008 |
| EP | 1734360 B1 | 5/2014 |
| JP | 3932368 B2 | 6/2007 |
| JP | 2009-281794 A | 12/2009 |
| JP | 2011-180045 A | 9/2011 |
| JP | 2012-185064 A | 9/2012 |
| WO | 2008/044037 A1 | 4/2008 |
| WO | 2013/039189 A1 | 3/2013 |
| WO | 2013/132706 A1 | 9/2013 |
| WO | 2013/177560 A1 | 11/2013 |

OTHER PUBLICATIONS

Zhang et al., "Manipulations of microfluidic droplets using electrorheological carrier fluid," Physical Review E (Statistical, Nonlinear, and soft matter physics), 78: 066305-1-066305-5 (2008).
Drenckhan et al., "Bubble size control and measurement in the generation of ferrofluid foams," Journal of Applied Physics, 93: 10078-10083 (2003).
Vojtisek et al., "Microfluidic devices in superconducting magnets: on-chip free-flow diamagnetophoresis of polymer particles and bubbles," Microfluidics and Nanofluidics, 13: 625-635 (2012).
Partial European Search Report issued in corresponding European Patent Application No. 15157032.2 dated Jul. 29, 2015.

* cited by examiner

CHIP FOR PLASMA GENERATION, PLASMA GENERATOR, AND PLASMA SPECTROMETRY METHOD

TECHNICAL FIELD

The present invention relates to a chip for plasma generation, a plasma generator, and a plasma spectrometry method.

BACKGROUND ART

The patent literature discloses a plasma generator for generating air bubbles in a channel that includes a narrow portion, further causing plasma to generate in the air bubbles, and measuring the resulting light emission. In patent literature 1, plasma in the narrow portion of the channel is measured, and in patent literature 2, plasma in a region other than the narrow portion is measured. However, in each of the described devices, there is a problem because the reproducibility of the plasma light emission is low.

CITATION LIST

Patent Literatures

Patent Literature 1: Japanese Patent No. 3932368
Patent Literature 2: JP 2012-185064 A

SUMMARY OF INVENTION

Technical Problem

The present invention is intended to provide a chip for plasma generation, a plasma generator, and a plasma spectrometry method, having high reproducibility of plasma light emission, for example.

Solution to Problem

In order to achieve the aforementioned objectives, the chip for plasma generation of the present invention comprises a channel that preserves a conductive solution, where the channel has a first region, a narrow portion, and a second region from the upstream side toward the downstream side, where the narrow portion is in communication with the first region and the second region and has a cross-sectional area smaller than the first region and the second region, and the chip further includes an air bubble movement prevention unit that prevents air bubbles generated in the narrow portion from moving from the narrow portion toward the upstream side of the narrow portion.

The plasma generator of the present invention includes a voltage application unit and the chip for plasma generation of the present invention.

The plasma spectrometry method of the present invention comprises: an electric field application step of applying a voltage to an electrode system including a pair of electrodes to apply an electric field to a channel containing a conductive solution supplied therein, thereby generating plasma in air bubbles generated in the channel; and a detection step of detecting plasma light emission generated in the channel, where the channel has a first region, a narrow portion, and a second region from the upstream side toward the downstream side, wherein the narrow portion is in communication with the first region and the second region and has a cross-sectional area smaller than the first region and the second region, wherein a cathode in the electrode system is arranged so as to be positioned on the upstream side of the narrow portion, wherein an anode in the electrode system is arranged so as to be positioned on the downstream side of the narrow portion, and movement of air bubbles generated in the narrow portion toward the upstream side of the narrow portion is prevented.

Advantageous Effects of Invention

The inventors of the present invention conducted earnest studies, and as a result, the inventors observed the following facts and achieved the present invention. The present invention, however, is not limited by the following description.

Plasma is generated at an interface between a gas (air bubbles) and a liquid (a conductive solution) (hereinafter referred to as a "gas-liquid interface"). In a conventional chip for plasma generation, air bubbles generated in the narrow portion move from the narrow portion toward the upstream side of the first region. Therefore, the gas-liquid interface is generated not in the narrow portion but in another region. Thus, the reproducibility is reduced in detection of plasma light emission in the narrow portion. That is, the present invention includes an air bubble movement prevention unit that inhibits the movement of air bubbles generated in the narrow portion from the narrow portion toward the upstream side of the narrow portion, and therefore, the formation of the gas-liquid interface in the narrow portion can be maintained, and thus, superior reproducibility of plasma light emission in the narrow portion can be achieved. Therefore, the present invention can perform an analysis with superior reliability and is useful in elemental analysis and the like utilizing plasma generation, for example.

BRIEF DESCRIPTION OF DRAWINGS

FIG. 1A is a top view. FIG. 1B is a cross-sectional view in the I-I direction of FIG. 1A. FIG. 1C is a cross-sectional view in the II-II direction of FIG. 1B. FIG. 1D is an enlarged view of a region (X) indicated by dashed lines of FIG. 1B. FIG. 1E is a cross-sectional view in the III-III direction of FIG. 1B.

DESCRIPTION OF EMBODIMENTS

1. Chip for Plasma Generation

Figure 1A:
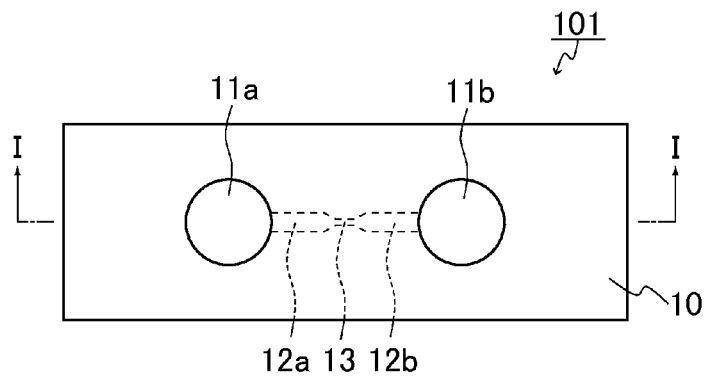
FIGS. 1A to 1E are schematic views showing an example of a chip for plasma generation according to the first embodiment of the present invention.

As mentioned above, the chip for plasma generation of the present invention comprises a channel that preserves a conductive solution, wherein the channel has a first region, a narrow portion, and a second region from the upstream side toward the downstream side, wherein the narrow portion is in communication with the first region and the second region and has a cross-sectional area smaller than the first region and the second region, and wherein the chip further includes an air bubble movement prevention unit that prevents air bubbles generated in the narrow portion from moving from the narrow portion toward the upstream side of the narrow portion.

The chip for plasma generation of the present invention achieves maintenance of the gas-liquid interface in the narrow portion by preventing the movement of air bubbles from the narrow portion toward the upstream side of the narrow portion. Therefore, the form of the air bubble movement prevention unit is not particularly limited as long as the movement of the air bubbles from the narrow portion toward the upstream side of the narrow portion can be prevented. The "movement of air bubbles" is an objective to be prevented in the present invention means the "movement of the gas-liquid interface on the upstream side, formed by air bubbles generated in the narrow portion".

It is preferred that the first region in the chip for plasma generation of the present invention has the air bubble movement prevention unit, for example.

In the chip for plasma generation of the present invention, as mentioned above, the channel has a first region, a narrow portion, and a second region from the upstream side, and each of these has a void (hollow), so that the inside of the regions are in communication with one another in this order. In the chip for plasma generation of the present invention, the direction from the first region toward the second region is referred to as the "longitudinal direction", the "axis direction", or the "electric field direction"; the first region side is referred to as the upstream side; and the second region side is referred to as the downstream side with a central focus on the narrow portion. The direction that is perpendicular to the longitudinal direction and is the plane direction is referred to as the "width direction", and the direction that is perpendicular to the longitudinal direction and is the vertical direction of the chip is referred to as the "height direction" or the "depth direction". The distance in the longitudinal direction is referred to as the "length", the distance in the width direction is referred to as the "width", and the distance in the height direction is referred to as the "height". The "cross-sectional area" in the channel means a cross-sectional area of the void inside the channel in the width direction (the direction perpendicular to the longitudinal direction), unless otherwise shown.

The shape of the channel is not particularly limited, and examples of the shape of the cross section of the channel include: a circular shape such as a circle, an exact circle, or an ellipse; a semicircular shape; and a polygonal shape such as a triangle, a quadrangle, a square, or a rectangle. In the channel, the first region, the narrow portion, and the second region may have different cross-sectional shapes, for example.

In the chip for plasma generation of the present invention, the narrow portion is a region having a cross-sectional area smaller than the first region and the second region and is preferably a region having a cross-sectional area significantly smaller than the first region and the second region. It is preferred that the narrow portion is specifically a region with a central focus on a portion having the smallest cross-sectional area in the channel. It is preferred that the narrow portion has an almost constant cross-sectional area over the full length thereof, for example. "The narrow portion having an almost constant cross-sectional area" also encompasses the meaning of a region having a cross-sectional area gradually increased toward the upstream side and the downstream side in the longitudinal direction with a central focus on a portion having the smallest cross-sectional area in addition to the meaning of a region having a completely constant cross-sectional area, for example. The cross-sectional area may be successively or non-successively increased, for example. In this case, the narrow portion is a successive region having cross-sectional areas of 50,000× or less, 1000× or less, 500× or less, or 100× or less relative to the smallest cross-sectional area, for example.

The cross-sectional area of the narrow portion may be set by narrowing the width, reducing the height, or both, relative to the first region and the second region.

The cross-sectional areas of the first region and the second region are, for example, more than 1×, 3× or more, 10× or more, 30× or more, 100× or more relative to the smallest cross-sectional area in the narrow portionx. The upper limit thereof is not particularly limited and is, for example, 10,000× or less, 8000× or less, or 5000× or less.

In the chip for plasma generation of the present invention, the chip itself may include an electrode, or a device in which the chip is set may include an electrode, for example. In the chip for plasma generation of the present invention, a pair of electrodes, i.e., a cathode and an anode may be arranged so that the narrow portion is positioned between the cathode and the anode in use, for example. Specifically, for example, the chip itself may include a pair of electrodes (electrode system) including an anode and a cathode; the chip itself may include a cathode, and a device in which the chip is set may include an anode; or the chip itself may include an anode, and a device in which the chip is set may include a cathode. In the case where the device includes an electrode, the electrode is, for example, preferably a solid electrode in which the chip can be inserted and can be a bar electrode or the like as a specific example.

In the chip for plasma generation of the present invention, the cathode is preferably arranged on the upstream side with a central focus on the narrow portion, more preferably arranged in the first region.

In the case where the chip itself includes the cathode, the cathode is preferably fixed to the inner wall of the first region, for example. By fixing the cathode on the inner wall of the first region, further superior reproducibility of plasma light emission can be achieved, for example.

In the case where the cathode is a fixed electrode, the cathode may be an electrode formed by coating the inner wall of the first region with a conductive material or an electrode formed by burying a conductive material in the inner wall of the first region, for example.

In the first region, a portion on which the cathode is fixed (hereinafter also referred to as a cathode fixation portion) is not particularly limited, and it is preferred that the end on the downstream side of the cathode fixation portion (end on the narrow portion side) is a portion near the narrow portion. The distance between the end on the downstream side of the cathode fixation portion in the first region and the end on the upstream side of the narrow portion (end on the first region side) is, for example, from 0 to 5 mm, from 0.3 to 3 mm, or from 1 to 3 mm in the longitudinal direction. The end on the upstream side of the cathode fixation portion is not particularly limited and may be, for example, the end on the upstream side of the first region. The cathode may be, for example, fixed to the entire inner wall of the first region.

In the chip for plasma generation of the present invention, the anode is preferably arranged on the downstream side with a central focus on the narrow portion, more preferably arranged in the second region. In the case where the chip itself includes the anode, the anode is, for example, preferably fixed to the inner wall of the second region.

In the case where the anode is a fixed electrode, as in the cathode, the anode may be an electrode formed by coating the inner wall of the second region with a conductive material or an electrode formed by burying a conductive material in the inner wall of the second region. A portion on which the anode is fixed is not particularly limited and can be described with reference to the description of the cathode by reading the "first region" as the "second region", the "upstream side" as the "downstream side", and the "downstream side" as the "upstream side", for example.

The material of the electrode is not particularly limited as long as it is a solid conductive material, with examples thereof including platinum, gold, carbon, zinc, brass, copper, stainless steel, iron and the like. The material of the cathode is, for example, preferably carbon, and the material of the anode is, for example, preferably carbon.

A method for forming an electrode by coating with a conductive material is not particularly limited, and a conventionally known method such as sputtering can be employed.

The chip for plasma generation of the present invention preferably further includes a first reservoir and a second reservoir which preserve a conductive solution. In this case, for example, one end of the first region is in communication with the narrow portion, the other end of the first region is in communication with the first reservoir, one end of the second region is in communication with the narrow portion, and the other end of the second region is in communication with the second reservoir. In the chip for plasma generation of the present invention, the cathode may be arranged in the first reservoir, for example, and the anode may be arranged in the second reservoir, for example. In this case, as mentioned above, the chip itself may include an electrode, or a device in which the chip is set may include an electrode.

In the case where the cathode and the anode are fixed electrodes such as mentioned above, the cathode may be fixed to the entire inner wall of the first reservoir, and the anode may be fixed to the entire inner wall of the second reservoir, for example.

The shapes and the sizes of the first reservoir and the second reservoir are not particularly limited as long as they can preserve a conductive solution. The shapes of the first reservoir and the second reservoir are not particularly limited, and examples thereof include a polygonal prism shape such as a triangular prism or a quadrangular prism, a cylindrical shape such as an exact cylinder or an elliptic cylinder, a conical shape, and the like.

The material of the chip for plasma generation of the present invention is not particularly limited, and for example, it is preferred that the inner wall of the chip except for the electrode is formed of an insulating material, and it is more preferred that the entire chip except for the electrode is formed of an insulating material. A method for producing the chip for plasma generation of the present invention is not particularly limited, and for example, a molded article having a channel and the like may be produced by injection molding or the like, or a channel and the like may be formed in a base material such as a plate. A method for forming a channel and the like is not particularly limited, and examples thereof include lithography and cutting.

The insulating material is not particularly limited, and examples thereof include a resin, silicone, glass, paper, ceramics, rubber, and the like. Examples of the resin include thermoplastic resins such as polyethylene, polypropylene, polystyrene, polyvinyl chloride, polyethylene terephthalate, polymethacrylate, polyamide, a saturated polyester resin, and an acrylic resin, epoxy resins such as an urea resin, a melamine resin, a phenol resin, a fluorine resin, and glass epoxy, and a thermosetting resin such as an unsaturated polyester resin. The silicone can be, for example, polydimethylsiloxane.

The application of the chip for plasma generation of the present invention is not particularly limited, and for example, the chip can cause a conductive solution to be supplied to the channel, an electric field to be applied to the channel by applying a voltage to an electrode system, plasma to be generated in the channel, for example. By detecting light emission caused by the plasma, a sample contained in the conductive solution can be analyzed, for example. When analysis is performed using the chip for plasma generation of the present invention as described above, the chip for plasma generation of the present invention can also be referred to as a chip for plasma light emission analysis.

The conductive solution can be, for example, a liquid sample and may further contain an electrolyte for imparting conductivity. Examples of the electrolyte include nitric acid, acetic acid, hydrochloric acid, lithium hydroxide, sodium hydroxide, and potassium chloride, and among them, nitric acid is preferable because the effect on the analysis can be sufficiently avoided.

The liquid sample may be, for example, a sample of a liquid itself, or a sample containing a solid. Examples of the sample include a sample derived from a biological body, a sample derived from environment, a metal, a chemical substance, and a pharmaceutical. The sample derived from a biological body is not particularly limited, and examples thereof include urine, blood, hair, and an umbilical cord. Examples of the blood sample include erythrocyte, whole blood, serum, and plasma. Examples of the biological body include humans, nonhuman animals, and plants. Examples of the nonhuman animals include mammals except for humans, and fish and seafood. A sample derived from the environment is not particularly limited, and examples thereof include food, water, the ground, the atmosphere, and air. Examples of metals include heavy metals such as Bi (bismuth), Hg (mercury), Cd (cadmium), Pd (palladium), Zn (zinc), Tl (thallium), Ag (silver), and Pb (lead). Examples of chemical substances include reagents, pesticides, and cosmetics. Examples of foods include fresh food and processed food. Examples of water include drinking water, ground water, river water, seawater, and domestic wastewater.

In the case where a subject to be analyzed is a heavy metal, the liquid sample may contain a reagent for separating a heavy metal in the sample, for example. The reagent can be, for example, a chelating agent, an acid, or an alkali, and specific examples thereof include dithizone, thiopronine, meso-2,3-dimercapto succinic acid (DMSA), sodium hydroxide, lithium hydroxide, 1,2-dimercapto-1-propanesulfonic acid sodium salt (DMPS), nitric acid, succinic acid, glycine, and cysteine.

The chip for plasma generation of the present invention is described below with reference to the first embodiment, the second embodiment, and the third embodiment as specific examples. The present invention, however, is not limited by these examples. Each of the embodiments can be described with reference to the description of each of the other embodiments, and the present invention may be in a form satisfying any one of, any two of, or all of the first to third embodiments.

(1) First Embodiment

The chip for plasma generation of the present embodiment is in a form in which the first region includes an air bubble movement prevention unit, specifically in the form in which the first region has, as the air bubble movement prevention unit, a cross-sectional area which inhibits the movement of air bubbles generated in the narrow portion toward the upstream side of the first region. As mentioned above, the shape of the channel is not particularly limited, and examples thereof include a circular shape, a semicircular shape, and a polygonal shape. Each of the shapes is not limited as long as it has a cross-sectional area which inhibits the movement of air bubbles generated in the narrow portion toward the upstream side. The cross-sectional area which inhibits the movement of air bubbles toward the upstream side is, for example, from 1 to 900,000,000 $\mu m^2$, from 1,000 to 50,000,000 $\mu m^2$, from 6,000 to 2,000,0000 $\mu m^2$. When the chip for plasma generation is used, a cathode is arranged on the first region side, and an anode is arranged on the second region side with a central focus on the narrow portion.

In the chip for plasma generation of the present embodiment, it is preferred that the upper surface of the first region is arranged at a height which inhibits the movement of air bubbles generated in the narrow portion toward the upstream side of the first region, from the bottom surface of the first region.

In the chip for plasma generation of the present embodiment, for example, it is preferred that the upper surface of the first region has a tapered portion and a parallel portion, the tapered portion is enlarged in the height direction from the end on the upstream side of the narrow portion toward the upstream side of the first region relative to the bottom surface of the first region, and the parallel portion is parallel with the bottom surface of the first region from the end on the upstream side of the tapered portion toward the upstream side of the first region.

In the conventional chip for plasma generation, in the inside of the first region, the bottom surface is horizontal, and the upper surface has a tapered region tilted from the end on the narrow portion side toward the end on the upstream side so as to increase an inner height. When the upper surface has a tapered shape, air bubbles generated in the narrow portion rapidly move from the narrow portion toward the upstream side of the first region along the slope of the tapered region. Therefore, air bubbles generated in the narrow portion move from the narrow portion toward the upstream side of the first region, and thus, the gas-liquid interface cannot be maintained in the narrow portion. In contrast, in the chip for plasma generation of the present embodiment, for example, the bottom surface and the upper surface inside the first region are parallel with each other, and therefore, the movement of air bubbles along the slope of the tapered region such as mentioned above is also suppressed, and the narrow portion can hold air bubbles. Thus, reproducibility of plasma light emission in the narrow portion can be improved.

In the present embodiment, it is preferred that the bottom surface and the upper surface inside the first region are horizontal planes. When the bottom surface and the upper surface are horizontal planes, the movement of the air bubbles can be further suppressed. The bottom surface and the upper surface being horizontal planes mean, for example, the bottom surface and the upper surface positioned in the horizontal direction when the chip for plasma generation is arranged in a horizontal position.

The length in the perpendicular direction between the bottom surface and the upper surface inside the first region (i.e., the inner height) is, for example, 1× or from more than 1× to 10,000×, 1× or from more than 1× to 1000×, 1 time or from more than 1× to 300× relative to the length in the perpendicular direction between the bottom surface and the upper surface inside the narrow portion (i.e., the inner height or the inner depth).

In the present embodiment, the shape and the size of the second region are not particularly limited.

A specific example of the chip for plasma generation of the present embodiment is described with reference to the schematic views of FIGS. 1A to 4. The present invention, however, is not limited by the following example. In the drawings, the identical parts are denoted by identical reference numerals, and the present embodiment can be described with reference to the description of each of the other embodiments, unless otherwise shown. There is a case where the structure of each portion is simplistically shown as appropriate in the drawings as a matter of convenience of the description, so that there is a case where the size, the proportion, and the like of each portion are different from the actual size, proportion, and the like, and the drawings are schematically shown.

FIG. 1A is a top view of a chip 101 for plasma generation. FIG. B is a cross-sectional view in the I-I direction of FIG. 1A. FIG. 1C is a cross-sectional view in the II-II direction of FIG. 1B. FIG. 1D is an enlarged view of a region (X) indicated by dashed lines of FIG. 1B. FIG. 1E is a cross-sectional view in the III-III direction of FIG. 1B.

Figure 1B:
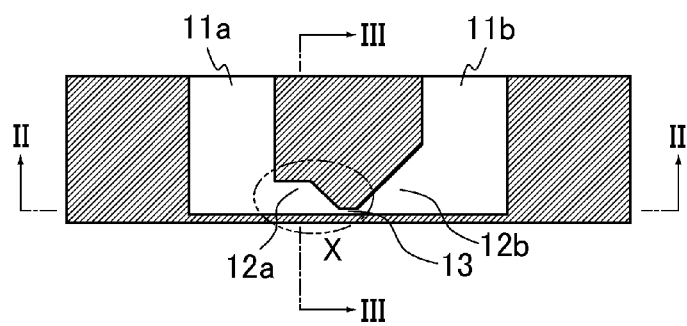
Figure 1C:
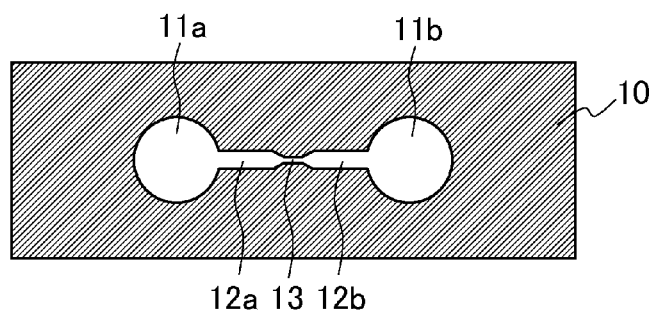
Figure 1D:
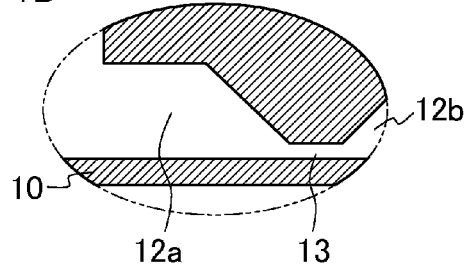
Figure 1E:
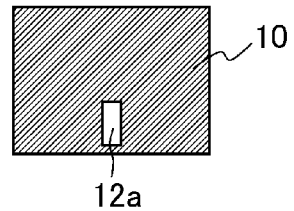

As shown in FIGS. 1A to 1E, the chip 101 for plasma generation includes a base material 10 including a channel, a first reservoir 11a, and a second reservoir 11b formed therein. In FIGS. 1A to 1E, the direction connecting between the first reservoir 11a and the second reservoir 11b, i.e., the crosswise direction in FIG. 1A is the longitudinal direction of the chip 101, the first reservoir 11a side is the upstream side, and the second reservoir 11b side is the downstream side. In FIGS. 1A to 1E, the direction perpendicular to the longitudinal direction in the upper surface of the chip 101, i.e., the lengthwise direction in FIG. 1A is the width direction of the chip 101. In FIGS. 1A to 1E, the direction perpendicular to the longitudinal direction in the cross section of the chip 101, i.e., the lengthwise direction in FIG. 1B is the height direction of the chip 101. The base material 10 has, as a channel, in this order, a first region 12a, a narrow portion 13, and a second region 12b inside of which are in communication with one another, the end on the upstream side of the first region 12a is in communication with one end of the first reservoir 11a, and the end on the downstream side of the second region 12b is in communication with one end of the second reservoir 11b. In the channel, the portion with the narrowest width is the center of the narrow portion 13. Each of the first reservoir 11a and the second reservoir 11b is a concave portion having a cylindrical shape, provided in the height direction of the base material 10 and is opened to the upper surface of the base material 10. In the chip 101 for plasma generation, the bottom surface inside the channel is a horizontal plane.

Relative to the length of the channel, i.e., the length from the end on the upstream side of the first region 12a toward the end on the downstream side of the second region 12b as 1, the length of the narrow portion 13 is, for example, from 1/1 to 1/10000, from 1/1 to 1/1000, or from 1/10 to 1/100.

The length of the channel, i.e., the length from the end on the upstream side of the first region 12a toward the end on the downstream side of the second region 12b is, for example, from 1 to 50 mm, from 1 to 10 mm, or from 3 to 7 mm, the length of the narrow portion 13 is, for example, from 1 to 1000 µm, from 1 to 600 µm, or from 1 to 400 µm. The lengths of the first region 12a and the second region 12b are, for example, from 1 to 50 mm, or from 1 to 10 mm.

As shown in FIGS. 1A to 1C, in the channel, each of the first region 12a, the narrow portion 13, and the second region 12b has an almost constant width. The width of the first region 12a is increased from the connection portion with the narrow portion 13 as a starting point toward the upstream side so as to have a tapered shape and is maintained to be constant from the position at which the width reaches a constant width toward the further upstream side. Similarly, the width of the second region 12b also is increased from the connection position with the narrow portion 13 as a starting point toward the downstream side so as to have a tapered shape and is maintained to be constant from the position at which the width reaches a constant width toward the further downstream side.

The width of the narrow portion 13 is, for example, from 1 to 2000 µm, from 100 to 500 µm, or from 200 to 300 µm and is, for example, from 1 to 2000 times, from 1 to 500 times, or from 200 to 300 times relative to the narrowest width. Each of the widths of the first region 12a and the second region 12b is, for example, from 10 to 5000 µm, from 100 to 2000 µm, or from 300 to 1000 µm and is, for example, from 1 to 5000 times, from 100 to 2000 times, or from 300 to 1000 times relative to the narrowest width of the narrow portion.

As shown in FIGS. 1B and 1D, in the channel, the narrow portion 13 has an almost constant inner height (depth). The inner height of the narrow portion 13 is, for example, from 1 to 1000 µm, from 10 to 500 µm, or from 30 to 100 µm.

As shown in FIGS. 1B and 1D, the first region 12a has a parallel region having a constant inner height in which the bottom surface and the upper surface are parallel with each other. As shown in FIGS. 1B and 1D, the upper surface of the first region 12a may further have a tapered region tilted to have a tapered shape so that the inner height is increased form the connection position with the narrow portion 13 toward the parallel region. The first region 12a, however, is not limited to this form and may be, for example, a form having no tapered region and having a parallel region over the full length.

The inner height of the parallel region in the first region 12a is, for example, from 10 to 3000 µm, or from 10 to 1000 µm and is, for example, from 2 to 3000×, from 2 to 50×, or from 2 to 10× relative to the inner height of the narrow portion 13. The height of the parallel region in the first region 12a is, for example, from 1 to 5 mm, or from 1 to 2 mm. The end on the narrow portion 13 side of the parallel region is positioned from 0 to 10 mm, or from 0 to 3 mm from the end on the narrow portion 13 side of the first region 12a in the longitudinal direction, for example. The end on the first reservoir 11a side of the parallel region is positioned from 0 to 10 mm, or from 0 to 3 mm from the end on the narrow portion 13 side of the first region 12a in the longitudinal direction, for example.

When the upper surface of the first region 12a has a tapered region so that the inner height is increased, the angle of the tapered region is not particularly limited and is, for example from 5° to 90°, from 10° to 80°, or from 5° to 45° to the axis direction.

The shape and the size of the second region 12b are not particularly limited. As shown in FIGS. 1B and 1D, the upper surface of the second region 12b has a tapered region enlarged to have a tapered shape so that the inner height is increased from the connection position with the narrow portion 13 toward the second reservoir 11b. The second region 12b, however, is not limited by this, and the shape of the second region 12b may be, for example, a shape that is symmetrical to the first region 12a.

The inner height at the end on the second reservoir 11b of the second region 12b is, for example, from 10 to 5000 µm, or from 30 to 3500 µm, and the angle of the tapered region is, for example, from 10° to 90°, from 10° to 80°, or from 10° to 45° to the axis direction.

The cross-sectional area of the parallel region in the first region 12a is, for example, from 1 to 10,000×, from 1 to 5000×, or from 1 to 500×, and the cross-sectional area at the end on the second reservoir 11b side of the second region 12b is, for example, from 1 to 20,000×, or from 1 to 1000× relative to the cross-sectional area of the narrow portion 13 as 1.

As to each of the first reservoir 11a and the second reservoir 11b, the diameter is, for example, from 1 to 5 mm, from 2 to 3.5 mm, and the height is, for example, from 0.5 µm to 10 mm, or from 2 to 6 mm.

The chip 101 for plasma generation can be used by setting it in a plasma generator including a voltage application unit and a detection unit, for example. In this case, the plasma generator or the chip 101 for plasma generation may include an electrode system to which a voltage is applied. In the former case, a cathode and an anode in the plasma generator may be inserted into a position at which the chip 101 for plasma generation is applied. As a specific example, it is preferred that the tip of the cathode is inserted into, for example, a position on the upstream side of the narrow portion 13, preferably the first region 12a in the chip 101 for plasma generation, and the tip of the anode is inserted into, for example, a position on the downstream side of the narrow portion 13, preferably the second region 12b in the chip 101 for plasma generation.

Then, a voltage is applied to the electrode system by the voltage application unit in the plasma generator, so that an electric field is applied to the chip 101 for plasma generation, air bubbles are generated, and plasma is generated from the air bubbles. Then, the generated plasma light emission is detected by the detection unit in the plasma generator.

Figure 2:
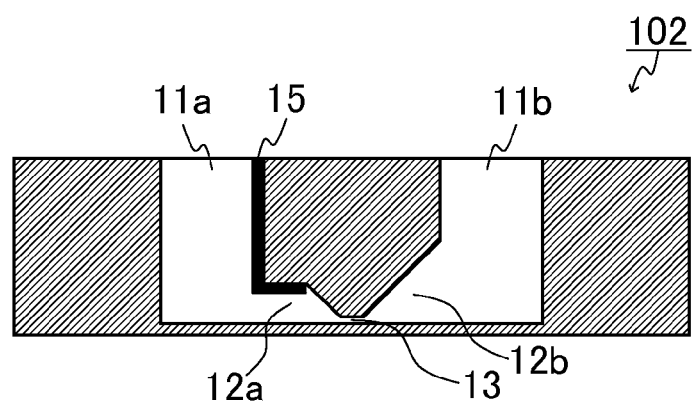
FIG. 2 is a cross-sectional view showing an example of the chip for plasma generation according to the first embodiment of the present invention.
Figure 3:
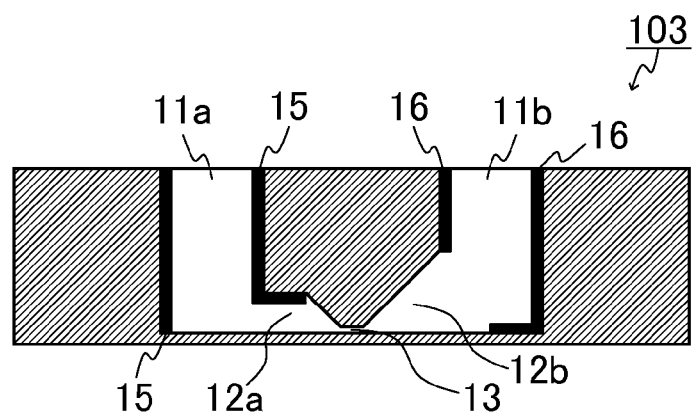
FIG. 3 is a cross-sectional view showing another example of the chip for plasma generation according to the first embodiment of the present invention.

The chip for plasma generation of the present embodiment may further include electrodes as mentioned above, for example. An example of the chip for plasma generation including electrodes is shown in the schematic views of FIGS. 2 and 3. FIGS. 2 and 3 are cross-sectional views in the same direction (I-I direction) as in FIG. 1B and are the same as FIG. 1B, unless otherwise shown.

As shown in FIG. 2, the chip 102 for plasma generation is in a form in which a cathode 15 is fixed on the inside (inner wall) of the first region 12a. Specifically, the cathode 15 is fixed from the inner wall of the first region 12a toward the inner wall of the first reservoir 11a so as to have a successive shape.

As to the cathode 15, the width is, for example, from 1 µm to 5 mm, from 1 µm to 3 mm, or from 1 µm to 1 mm, the thickness is, for example, from 0.1 angstrom to 1000 µm, from 0.1 angstrom to 100 µm, or from 0.1 angstrom to 40 µm, and the position of the tip of the cathode 15 is, for example, from 1 µm to 5 mm, from 1 µm to 3 mm, or from 1 µm to 1 mm, from the end on the downstream side of the first region 12a (end on the narrow portion 13 side).

As shown in FIG. 3, in the chip 103 for plasma generation, the cathode 15 is fixed on the inner walls of the first reservoir 11a and the first region 12a, and the anode 16 is fixed on the inner walls of the second reservoir 11b and the second region 12b.

Figure 4:
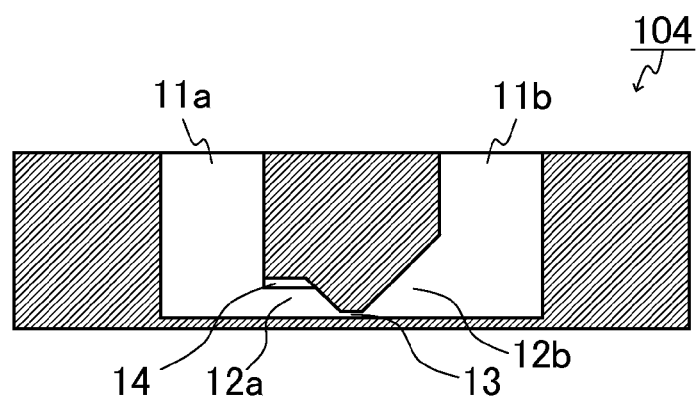
FIG. 4 is a cross-sectional view showing yet another example of the chip for plasma generation according to the first embodiment of the present invention.
Figure 5:
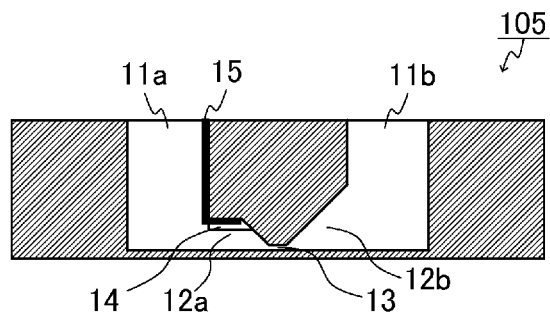
FIG. 5 is a cross-sectional view showing yet another example of the chip for plasma generation according to the first embodiment of the present invention.

In the chip for plasma generation of the present embodiment, the upper surface of the first region 12a may further have a grooved portion along the longitudinal direction, for example. An example of the chip for plasma generation including a grooved portion is shown in the schematic views of FIGS. 4 and 5. FIGS. 4 and 5 are cross-sectional views in the same direction (I-I direction) as in FIG. 1B and are the same as FIG. 1B, unless otherwise shown.

As shown in FIG. 4, in the chip 104 for plasma generation, the inner wall (upper surface) of the first region 12a has a grooved portion 14 along the longitudinal direction.

As shown in FIG. 5, in the chip 105 for plasma generation, an electrode may further be fixed on the grooved portion 14 of the first region 12a.

As shown in FIG. 5, the chip 105 for plasma generation is in a form in which a cathode 15 is fixed on the inside (inner wall) of a grooved portion 14 in the first region 12a. Specifically, the cathode 15 is fixed from the inner wall of the grooved portion 14 in the first region 12a toward the inner wall of the first reservoir 11a so as to have a successive shape.

(2) Second Embodiment

The chip for plasma generation of the present embodiment is in a form of having any of the following units (2-1) to (2-5) as the air bubble movement prevention unit. The present embodiment may include any one of the air bubble movement prevention units or two or more of the air bubble movement prevention units.
(2-1) The upper surface of the first region has, as the air bubble movement prevention unit, a concave portion that holds air bubbles.
(2-2) The upper surface of the first region has, as the air bubble movement prevention unit, a convex portion that holds air bubbles.
(2-3) The end on the upstream side of the first region has, as the air bubble movement prevention unit, an opening in a size in which air bubbles cannot pass through.
(2-4) The first region has, as the air bubble movement prevention unit, a partition through which a liquid passes and air bubbles cannot pass so as to be parallel with the height direction.
(2-5) The first region has, as the air bubble movement prevention unit, an air bubble adsorption unit that adsorbs air bubbles.

Specific examples of the chips for plasma generation having the air bubble movement prevention units (2-1) to (2-5), respectively, are described with reference to the schematic views of FIGS. 6A to 6F. The present invention, however, is not limited by the following examples. In the drawings, the identical parts are denoted by identical reference numerals, and the present embodiment can be described with reference to the description of each of the other embodiments, unless otherwise shown. There is a case where the structure of each portion is simplistically shown as appropriate in the drawings as a matter of convenience of the description, so that there is a case where the size, the proportion, and the like of each portion are different from the actual size, proportion, and the like, and the drawings are schematically shown. FIGS. 6A to 6F show a region X in FIG. 1B and is the same as FIGS. 1A to 1E, unless otherwise shown.

Figure 6A:
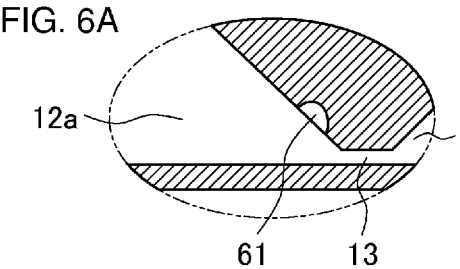
FIGS. 6A to 6F are cross-sectional views each showing an example of the chip for plasma generation according to the second embodiment of the present invention.
Figure 6B:
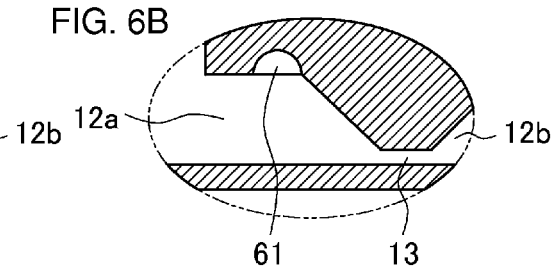

The form (2-1), i.e., the form in which the upper surface inside the first region has, as the air bubble movement prevention unit, a concave portion that holds air bubbles is shown in FIGS. 6A and 6B.

As shown in FIGS. 6A and 6B, the chip for plasma generation of the present embodiment is in a form in which the upper surface of the first region 12a has a concave portion 61. In the case of FIG. 6A, the concave portion 61 serves as a portion into which air bubbles are drawn. Specifically, for example, even when air bubbles generated in the narrow portion 13 move from the narrow portion 13 toward the first region 12a side, the air bubbles are drawn into the concave portion 61, and thus, the movement of the air bubbles can be inhibited. Thus, the gas-liquid interface in the narrow portion can be maintained. In the case of FIG. 6B, the concave portion 61 serves as a portion in which air bubbles are preserved. Specifically, for example, when air bubbles generated in the narrow portion 13 move from the narrow portion 13 toward the first region 12a side, the air bubbles enter the concave portion 61, and thus, the movement of the air bubbles can be inhibited. Thus, the gas-liquid interface in the narrow portion can be maintained.

In FIG. 6A, the shape of the concave portion 61 is, for example, an ellipse, an exact circle, or a circle. In FIG. 6B, the shape of the concave portion 61 is, for example, a bowl shape.

Figure 6C:
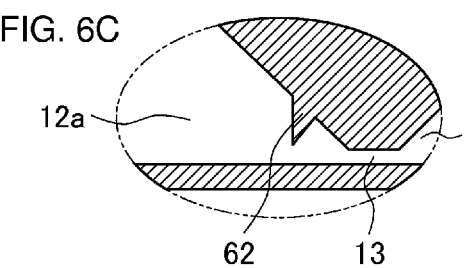

The form (2-2), i.e., the form in which the upper surface inside the first region has, as the air bubble movement prevention unit, a convex portion that holds air bubbles is shown in FIG. 6C.

As shown in FIG. 6C, the chip for plasma generation of the present embodiment is in a form in which the upper surface of the first region 12a has, as the air bubble movement prevention unit, a convex portion 62. In the case of FIG. 6C, the convex portion 62 serves as a portion into which air bubbles are drawn. Specifically, for example, even when air bubbles generated in the narrow portion 13 move from the narrow portion 13 toward the first region 12a side, the air bubbles are drawn into the convex portion 62, and thus, the movement of the air bubbles can be inhibited. Thus, the gas-liquid interface in the narrow portion can be maintained.

In FIG. 6C, the shape of the convex portion 62 is, for example, a polygonal shape such as a triangle or a quadrangle.

Figure 6D:
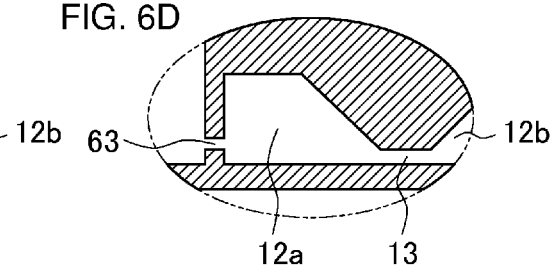

The form (2-3), i.e., the form in which the end on the upstream side of the first region has an opening in a size in which air bubbles cannot pass through is shown in FIG. 6D.

As shown in FIG. 6D, the chip for plasma generation of the present embodiment is in a form in which the end on the upstream side of the first region 12a has an opening 63 in a size in which air bubbles cannot pass through. In the case of FIG. 6D, the opening 63 substantially serves as a plug that inhibits air bubbles from passing through. Specifically, for example, even when air bubbles generated in the narrow portion 13 move from the narrow portion 13 toward the first region 12a side, the air bubbles cannot pass through the opening 63, and thus, the movement of the air bubbles can be inhibited. Thus, the gas-liquid interface in the narrow portion can be maintained.

In FIG. 6D, the shape of the opening 63 can be, for example, a polygonal shape such as a triangle, or a quadrangle or a circle, and as the size of the opening 63, the opening 63 has a cross-sectional area preferably larger than the narrow portion, for example.

Figure 6E:
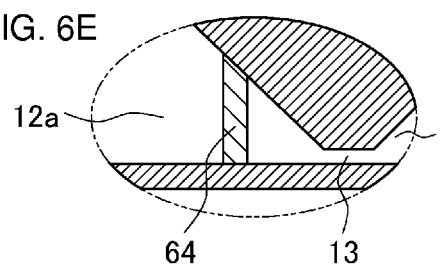

The form (2-4), i.e., the form in which the first region 12a has, as the air bubble movement prevention unit, a partition through which a liquid passes and air bubbles cannot pass, arranged therein so as to be parallel with the height direction, is shown in FIG. 6E.

As shown in FIG. 6E, the chip for plasma generation of the present embodiment is in a form in which the inside of the first region 12a has a partition (member) 64 through which a liquid passes and air bubbles cannot pass, arranged therein so as to be parallel with the height direction. In the case of FIG. 6E, the member 64 serves as a wall that inhibits the movement of air bubbles. Specifically, for example, even when air bubbles generated in the narrow portion 13 move from the narrow portion 13 toward the first region 12a side, the air bubbles cannot pass through the partition 64, and thus, the movement of the air bubbles can be inhibited. Thus, the gas-liquid interface in the narrow portion can be maintained.

In FIG. 6E, the partition 64 is not particularly limited, and examples thereof include a porous body, a woven fabric, and a nonwoven fabric. The material of the partition 64 is, for example, a resin, paper, glass, or the like.

The form (2-5) is a form of having, as the air bubble movement prevention unit, an air bubble adsorption unit that adsorbs air bubbles. The air bubble adsorption unit can be formed by arranging a member that physically or chemically adsorbs air bubbles, for example. It is preferred that the air bubble adsorption unit is arranged in the upper surface inside the first region, for example. As a specific example, a form in which the air bubble adsorption unit is arranged in the upper surface inside the first region is shown in FIG. 6F.

Figure 6F:
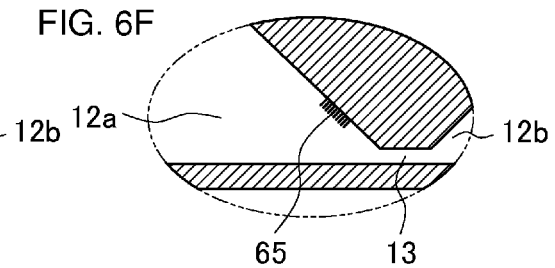

As shown in FIG. 6F, the chip for plasma generation of the present embodiment is in a form in which the upper surface of the first region 12a has an air bubble adsorption unit 65 arranged therein. In the case of FIG. 6E, specifically, for example, even when air bubbles generated in the narrow portion 13 move from the narrow portion 13 toward the first region 12a side, the air bubbles are captured in the air bubble adsorption unit 65, and thus, the movement of the air bubbles can be inhibited. Thus, the gas-liquid interface in the narrow portion can be maintained.

In FIG. 6E, the air bubble adsorption unit 65 is not particularly limited and is, for example, a porous body, a woven fabric, or a nonwoven fabric. The material of the air bubble adsorption unit 65 is, for example, a resin, paper, or glass.

The chip for plasma generation of the present invention encompasses, in addition to these embodiments, a form in which particles are arranged in the channel, a form in which a magnetic field is generated in the inner wall of the first region, and a form in which a magnet is arranged, for example.

(3) Third Embodiment

The chip for plasma generation of the third embodiment is in a form of having any of the following units (3-1) to (3-4) as the air bubble movement prevention unit. The present embodiment may have any one of or two or more of the air bubble movement prevention units, for example.
(3-1) The air bubble movement prevention unit is an unit that increases the stress resistance or the viscosity of a conductive solution in the channel.
(3-2) The first region has, as the air bubble movement prevention unit, particles.
(3-3) The air bubble movement prevention unit is an unit that causes a conductive solution in the channel to be subjected to convection.
(3-4) The air bubble movement prevention unit is an unit that causes the first region to generate a magnetic field.

In (3-1), for example, as the conductive solution, a rheology fluid (rheology fluid: ER) whose stress resistance is increased by applying a voltage, a liquid whose stress resistance is increased by a shock such as explosion (plasmarization) of air bubbles, or a liquid having a high viscosity is preferable. By using such conductive solution, for example, the air bubbles generated in the narrow portion can be inhibited from moving toward the upstream side of the first region.

In (3-2), the particles are not particularly limited, and examples thereof include chelating agent particles and magnetic particles.

In (3-3), an unit for convection is not particularly limited as long as a conductive solution in the channel can be subjected to convection.

In (3-4), an unit that generates a magnetic field is not particularly limited, and for example, a magnet such as a SmFEN cylindrical bond magnet, an air core coil, or a neodymium magnet can be used.

2. Plasma Generator

The plasma generator of the present invention includes, as mentioned above, a voltage application unit and the chip for plasma generation of the present invention. The plasma generator of the present invention is characterized in that it includes the chip for plasma generation, and the other configurations and conditions are not particularly limited. The plasma generator of the present invention can be described with reference to the description of the chip for plasma generation of the present invention, unless otherwise shown.

The plasma generator of the present invention can analyze a sample by generating plasma and detecting light emission caused by the plasma, for example. Therefore, the plasma generator of the present invention can also be referred to as a plasma spectrophotometer, for example.

The plasma generator of the present invention preferably further includes a detection unit that detects plasma light emission generated in the chip for plasma generator, for example. The detection unit is, for example, an unit that detects plasma light emission generated in the narrow portion of the channel in the chip for plasma generation of the present invention, for example.

A region to be detected by the detection unit is not particularly limited and may be, for example, in the chip for plasma generation of the present invention, only the narrow portion or a region including the narrow portion (a region including the narrow portion and another region). The center of the region to be detected is not particularly limited, and for example, in the chip for plasma generation of the present invention, the center of the narrow portion may be set as a central point, a portion moved from the center of the narrow portion toward the upstream side or the downstream side in the longitudinal direction may be set as the central point. As a specific example, for example, the region to be detected is preferably only the narrow portion with the center of the narrow portion as the central point.

3. Plasma Spectrometry Method

As mentioned above, the plasma spectrometry method of the present invention includes: an electric field application step of applying a voltage to an electrode system including a pair of electrodes to apply an electric field to a channel containing a conductive solution supplied therein, thereby generating plasma in air bubbles generated in the channel; and a detection step of detecting plasma light emission generated in the channel, the channel has a first region, a narrow portion, and a second region from the upstream side toward the downstream side, the narrow portion is in communication with the first region and the second region and has a cross-sectional area smaller than the first region and the second region, a cathode in the electrode system is arranged so as to be positioned on the upstream side of the narrow portion, an anode in the electrode system is arranged so as to be positioned on the downstream side of the narrow portion, and movement of air bubbles generated in the narrow portion toward the upstream side of the narrow portion is prevented.

The plasma spectrometry method of the present invention achieves the maintenance of the gas-liquid interface in the narrow portion by preventing the movement from the narrow portion toward the upstream side of the narrow portion as in the chip for plasma generation of the present invention. Therefore, in the present invention, a method for preventing the movement of the air bubbles is not particularly limited as long as the movement of the air bubbles from the narrow portion toward the upstream side of the narrow portion is prevented.

In the plasma spectrometry method of the present invention, for example, the chip for plasma generation of the present invention or the plasma generator of the present invention can be used, for example. The plasma spectrometry method of the present invention can be described with reference to the descriptions of the chip for plasma generation and the plasma generator of the present invention, unless otherwise shown.

It is preferred that the movement of the air bubbles is prevented in the first region in the plasma spectrometry method of the present invention, for example.

The plasma spectrometry method of the present invention may further include the step of supplying the conductive solution to the channel. The conductive solution can be, for example, a liquid sample and may further contain an electrolyte for imparting conductivity. The electrolyte is, for example, the same as mentioned above, and among them, nitric acid is preferably because the influence on analysis can be sufficiently avoided, for example.

The liquid sample is the same as mentioned above, for example. In the case where the subject to be analyzed is a metal, the liquid sample may contain a reagent for separating the metal in the sample, for example. The reagent can be, for example, the same as mentioned above, for example.

In the plasma spectrometry method of the present invention, it is preferred that a liquid having a high stress resistance or a high viscosity is used as the conductive solution to inhibit the movement of air bubbles generated in the narrow portion toward the upstream side of the first region, for example. Examples of the liquid include a liquid whose stress resistance is increased by applying a voltage (rheology fluid: ER), a liquid whose stress resistance is increased by explosion of air bubbles (plasmarization), and a solution having a high viscosity.

In the plasma spectrometry method of the present invention, the conductive solution may be a solution containing particles for the same reason, for example. The particles may be introduced into the chip for plasma generation together with the conductive solution, or the channel in the chip for plasma generation contains the particles in advance. Examples of the particles include chelating agent particles and magnetic particles as mentioned above.

In the plasma spectrometry method of the present invention, the conductive solution in the channel may be subjected to convection in the channel in order to maintain the gas-liquid interface in the narrow portion, for example. By subjecting the conductive solution to convection, air bubbles cannot escape. Thus, the gas-liquid interface in the narrow portion can be maintained.

In the plasma spectrometry method of the present invention, a magnetic field may be generated in the first region. In the generation of a magnetic field, a magnet can be used, for example. By generating a magnetic field, air bubbles cannot escape. Thus, the gas-liquid interface in the narrow portion can be maintained.

In the plasma spectrometry method of the present invention, it is preferred that a cathode and an anode forming an electrode system are arranged so as to be partially or entirely in contact with the conductive solution. Moreover, it is preferred that the cathode is arranged on the upstream side of the narrow portion, and the anode is arranged on the downstream side of the narrow portion.

In the step of the voltage application, when an electric field is applied to a channel containing a conductive solution supplied therein by applying a voltage to an electrode system including a pair of electrodes, air bubbles are generated in the narrow portion, and plasma is generated in the generated air bubbles.

A voltage can be applied to the electrode system using a voltage application unit. The voltage application unit is not particularly limited as long as a voltage can be applied between the electrodes, and a voltage generator or the like can be used as a known unit. A voltage to be applied between the electrodes is not particularly limited and can be set appropriately according to the sizes of air bubbles to be generated, the size and conditions of plasma to be generated, the kind of the conductive solution, the lengths and sizes of the channel and the narrow portion, and the like, for example. The voltage can be set from 30 to 5000 V, from 100 to 1500 V, for example, and the current between the electrodes can be set from 0.1 to 1000 mA, from 2 to 100 mA, for example.

The intensity of the electric field in the channel is not particularly limited and can be set appropriately according to the kind of the conductive solution, the lengths and the sizes of the channel and the narrow portion, and the like, for example. The intensity of the electric field can be set from 0.01 to 100 MV/m, from 1 to 10 MV/m, for example.

A voltage may be applied between electrodes continuously or discontinuously, for example. The time to apply a voltage is, for example, in the case of continuous application, from 1 to 1000 ms per one time. In the case of discontinuous application, the number of applications of voltage is, for example, from 1 to 1000 times, from 10 to 50 times per 1 second, and the time to apply a voltage is, for example, from 1 µs to 500 ms, from 20 µs to 5 ms per one time.

In the detection step, light emission caused by plasma generated in the channel in the step of the voltage application is detected. In the detection step, a region to be detected in the channel is not particularly limited and is the same as mentioned above, and for example, it is preferred that plasma light emission generated in the narrow portion is detected.

The plasma spectrometry method of the present invention is described with reference to specific examples of the first embodiment, the second embodiment, and the third embodiment. The present invention, however, is not limited by these examples. Each of the embodiments can be described with reference to the description of each of the other embodiments, unless otherwise shown, and the present invention may be in a form of satisfying any one of, any two of, or all of the first to third embodiments.

(1) First Embodiment

The plasma spectrometry method of the present embodiment is in a form in which the movement of air bubbles is inhibited in the first region, specifically a form in which the first region has a cross-sectional area which inhibits the movement of air bubbles generated in the narrow portion toward the upstream side of the first region, thereby preventing the movement of the air bubbles. The present embodiment can be described with reference to the description of the chip for plasma generation of the first embodiment according to the present invention.

In the plasma spectrometry method of the present embodiment, for example, it is preferred that the upper surface of the first region is arranged at a height which inhibits the movement of air bubbles generated in the narrow portion toward the upstream side of the first region, from the bottom surface of the first region. It is also preferred that the upper surface of the first region has a tapered portion and a parallel portion, the tapered portion is enlarged in the height direction from the end on the upstream side of the narrow portion toward the upstream side of the first region relative to the bottom surface of the first region, and the parallel portion is parallel with the bottom surface of the first region from the end on the upstream side of the tapered portion toward the upstream side of the first region.

(2) Second Embodiment

In the plasma spectrometry method of the present embodiment, the channel is in a form in which the movement of the air bubbles is prevented by any of the followings (2-1') to (2-5'). In the present embodiment, any one of or two or more of (2-1') to (2-5') may be used in combination.
(2-1') The upper surface of the first region has a concave portion that holds air bubbles, thereby preventing the movement of the air bubbles.
(2-2') The upper surface of the first region has a convex portion that holds air bubbles, thereby preventing the movement of the air bubbles.
(2-3') The end on the upstream side of the first region has an opening in a size in which air bubbles cannot pass through, thereby preventing the movement of the air bubbles.
(2-4') The first region has a partition through which a liquid passes and air bubbles cannot pass so as to be parallel with the height direction, thereby preventing the movement of the air bubbles.
(2-5') Air bubbles are adsorbed, thereby preventing the movement of the air bubbles.

The present embodiment can be described with reference to the description of the chip for plasma generation of the second embodiment according to the present invention, and specifically, (2-1') to (2-5') can be described with reference to (2-1) to (2-5) in the chip for plasma generation of the second embodiment according to the present invention.

(3) Third Embodiment

The plasma spectrometry method of the present embodiment is in a form in which the movement of the air bubbles is prevented by any of the followings (3-1') to (3-4'). In the present embodiment, any one of or two or more of (3-1') to (3-4') may be used in combination, for example.
(3-1') The stress resistance or viscosity of a conductive solution in the channel is increased, thereby preventing the movement of the air bubbles.
(3-2') The first region has particles, thereby preventing the movement of the air bubbles.
(3-3') The conductive solution in the channel is subjected to convection, thereby preventing the movement of the air bubbles.
(3-4') A magnetic field is generated in the first region, thereby preventing the movement of the air bubbles.

The present embodiment can be described with reference to the description of the chip for plasma generation of the third embodiment according to the present invention, for example, and specifically, (3-1') to (3-4') can be described with reference to the (3-1) to (3-4) in the chip for plasma generation of the third embodiment according to the present invention.

In (3-3'), the convection of the conductive solution is not particularly limited and can be performed by the following method, for example. For example, when diluted hydrochloric acid (HCl) is mixed with the conductive solution, a chloride ion becomes a chloride gas on the anode (positive electrode) side, a hydrogen ion becomes a hydrogen gas on the cathode (negative electrode) side, and the concentration gradient is generated in each of the poles. At that time, when the current density is high, the convection of the conductive solution occurs. By this convection, the gas-liquid interface in the air bubbles can be fixed on the narrow portion. The gas-liquid interface in the air bubbles can be fixed using a propeller mechanism or a squirt mechanism, for example.

In (3-4'), the generation of the magnetic field is not particularly limited and can be performed by the following method, for example. For example, in the state where air bubbles are generated in the narrow portion, a magnetic field having an intense magnetic gradient is added, and a magnetic field force is applied to the air bubbles by the difference in bulk susceptibility between a liquid and gas, thereby fixing the gas-liquid interface in the air bubbles. For the generation of the intense magnetic gradient, a SmFEN cylindrical bond magnet, an air core coil, or a neodymium magnet can be used, for example.

The example of the present invention is described below. The present invention, however, is not limited by the following example.

EXAMPLE

Example 1

The reproducibility of plasma light emission was checked using the chip for plasma generation of the first embodiment according to the present invention.

(1) Chip for Plasma Generation

A chip 101 for plasma generation shown in FIGS. 1A to 1E was produced. Specifically, a plate of quartz glass as a lower substrate and a plate of polybutylene terephthalate (PBT, DURANEX®2002, manufactured by Polyplastic) as an upper surface were provided. A void shown in FIGS. 1A to 1E was formed in the upper substrate by a molding method, and the upper substrate and the lower substrate are then joined to each other with a ultraviolet curable adhesive. Thus, a chip 101 for plasma generation was produced.

The size of each portion of the chip 101 for plasma generation was set as follows.
  Narrow portion 13
    Length: 600 μm
    Width: 220 μm
    Height: 30 μm
  First region 12a
    Full length: 2.5 mm
    Width: 1 mm
    Length of tapered region in longitudinal direction: 2.5 mm
    Angle of tapered region: 45°
    Length of parallel region: 2 mm
    Height of parallel region: 1 mm
  Second region 12b
    Length: 2.5 mm
    Width: 1 mm
    Angle of tapered portion: 45°
  First reservoir 11a and second reservoir 11b
    Diameter: 3.2 mm
    Height: 6 mm
  Chip 101
    Full length: 35 mm
    Full width: 12 mm
    Height: 6 mm (2) Measurement of Plasma Light Emission Thiopronine was dissolved in nitric acid so as to have a final concentration of 500 mmol/L. Thus, a thiopronine sample was prepared. This was used as a conductive solution.

In the chip 101 for plasma generation, a cathode was inserted into a first reservoir 11a, and an anode was inserted into a second reservoir 11b. As the cathode and the anode, carbon electrode bars (DPP CRP microcarbon rod, diameter: 0.28 mm, manufactured by Sano Factory) were used. Subsequently, in the chip 101 for plasma generation, 80 μL of the conductive solution was introduced into the first reservoir 11a and was led out to the second reservoir 11b. Thus, the conductive solution was introduced into the first region 12a, the narrow portion 13, and the second region 12b.

Figure 7:
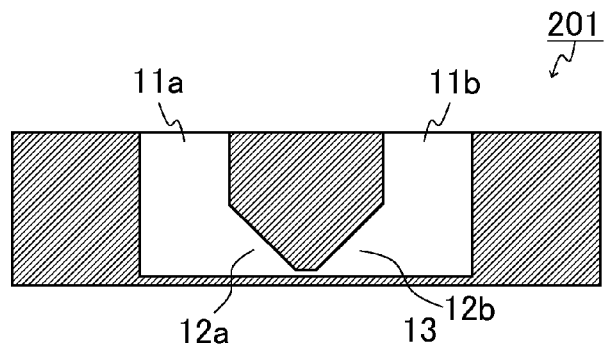
FIG. 7 is a cross-sectional view of the chip for plasma generation of a comparative example in Example 1 of the present invention.

Then, a voltage is applied between the cathode and the anode, and a light emission spectrum of plasma light emission in the narrow portion of the chip 101 for plasma generation was analyzed. For the detection of light emission, a charge-coupled device (CCD) was used. The conditions under which a voltage was applied (hereinafter referred to as the application conditions) and the conditions under which plasma light emission was analyzed (hereinafter referred to as the analysis conditions) were as follows. The light exposure time is the time in which a charge-coupled device (CCD) for use in detection of light emission is on. Based on CCD-ON in which light emission is detected and CCD-OFF in which light emission is not detected as one cycle, the cycle was performed a total 40 cycles (times). During CCD-ON in one cycle, application and non-application of a voltage were repeated, and based on one time of the application and the non-application as one set, the time in one set is referred to as the SW (switching) time, and the proportion (%) of the time of the application in one set is referred to as Duty.
  (Application Conditions)
    Applied voltage: 850 V
    Applied current: 850 mA
    Application time: 350 ms
    Exposure time: 150 ms
    SW time: 50 μs
    Duty: 16%
    The number of applications: 40 times at intervals of 5000 ms
  (Analysis Conditions)
    Analysis region: a region having a diameter of 400 μm with the center of the narrow portion as the central point
    Optical fiber: a single core having a diameter of 400 μm As a comparative example, a chip for plasma generation in which a first region has no parallel region and has a symmetric structure to a second region was subjected to the same analysis. FIG. 7 shows a cross-sectional view of the chip 201 for plasma generation of the comparative example.

Figure 8:
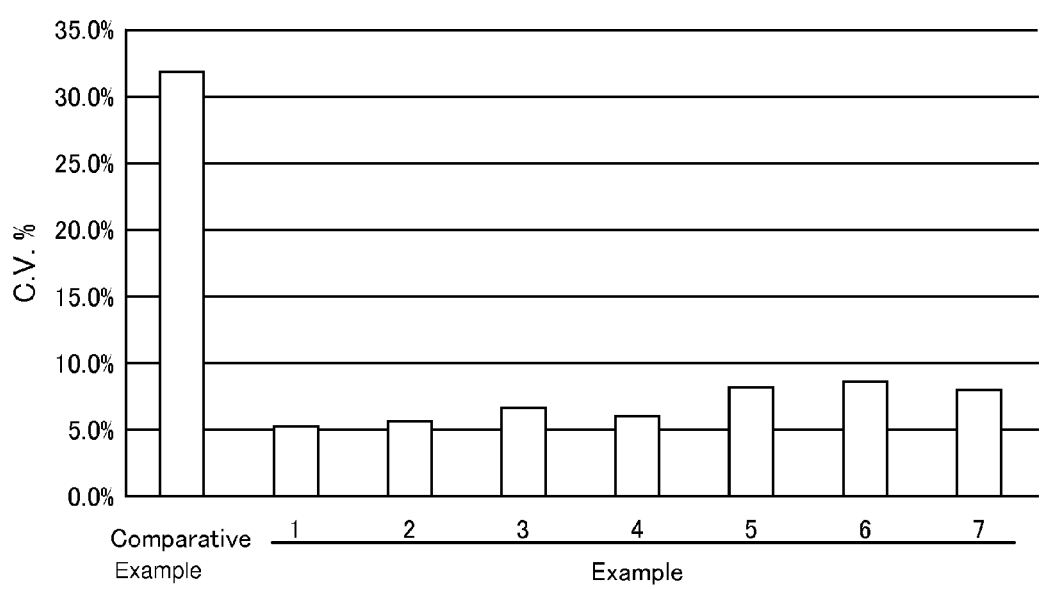
FIG. 8 is a graph showing the coefficient of variation (C.V.) value of the count value of plasma light emission in Example 1 of the present invention.

40 cycles of applications were performed at intervals of 5000 ms, analysis of light emission of the 40 cycles was performed, and then, the C.V. value was determined from count values of samplings of 21 to 40 cycles. Seven kinds (Nos. 1 to 7) of the chip for plasma generation having the same shape were produced, and the analysis was performed. The results of these are shown in FIG. 8. FIG. 8 is a graph showing the C.V. value of plasma light emission, and the vertical axis indicates the C.V. value.

As shown in FIG. 8, according to the chip 101 for plasma generation of the example, compared with the chip for plasma generation of the comparative example, variations in count value among samplings were small. Therefore, according to the chip for plasma generation of the first embodiment according to the present invention, a change in liquid resistance value between electrodes is suppressed, and the voltage to be applied to the channel can be stabilized. Thus, high reproducibility of plasma light emission can be achieved.

While the present invention has been particularly shown and described with reference to exemplary embodiments and examples thereof, the present invention is not limited to these embodiments and examples. It will be understood by those of ordinary skill in the art that various changes in form and details may be made therein without departing from the scope of the present invention.

This application claims priority from Japanese Patent Application No. 2014-39507 filed on Feb. 28, 2014 and from Japanese Patent Application No. 2015-33826 filed on Feb. 24, 2015, the entire subject matter of which are incorporated herein by reference.

INDUSTRIAL APPLICABILITY

According to the chip for plasma generation of the present invention, superior reproducibility of plasma light emission can be achieved. Therefore, the present invention is really useful in element analysis and the like utilizing plasma generation, for example.

REFERENCE SIGNS LIST 10 substrate
11a first reservoir
11b second reservoir
12a first region
12b second region
13 narrow portion
15 cathode
16 anode
101, 102, 103, 104, 105, 201 chip for plasma generation

The invention claimed is:

1. A plasma generator comprising:
a chip for plasma generation comprising:
   a channel configured to preserve a conductive solution,
   the channel comprises a first region, a narrow portion, and a second region from the upstream side toward the downstream side,
   the narrow portion is in communication with the first region and the second region and has a cross-sectional area smaller than the first region and the second region,
   a cathode in an electrode system is arranged so as to be positioned on the upstream side of the narrow portion,
   an anode in the electrode system is arranged so as to be positioned on the downstream side of the narrow portion, and
   the chip further comprises an air bubble movement prevention unit configured to prevent air bubbles generated in the narrow portion from moving from the narrow portion toward the upstream side of the narrow portion, wherein the upper surface of the first region contains the air bubble movement prevention unit as a concave portion configured to hold the air bubbles;
a voltage application unit; and
a detection unit configured to detect plasma light emission generated in the chip.

2. The chip according to claim 1, wherein the air bubble movement prevention unit is a cross-sectional area configured to inhibit movement of air bubbles generated in the narrow portion from the narrow portion toward the upstream side of the first region.

3. The chip according to claim 2, wherein the upper surface of the first region is arranged at a height which inhibits movement of air bubbles generated in the narrow portion from the narrow portion toward the upstream side of the first region, from the bottom surface of the first region.

4. The chip according to claim 2, wherein:
   the upper surface of the first region has a tapered portion and a parallel portion,
   the tapered portion is enlarged in the height direction from the end on the upstream side of the narrow portion toward the upstream side of the first region relative to the bottom surface of the first region, and
   the parallel portion is parallel with the bottom surface of the first region from the end on the upstream side of the tapered portion toward the upstream side of the first region.

5. A plasma spectrometry method comprising:
applying an electric field to a channel containing a conductive solution supplied therein, thereby generating plasma in air bubbles generated in the channel; and
detecting plasma light emission generated in the channel,
the channel comprises a first region, a narrow portion, and a second region from the upstream side toward the downstream side, wherein:
   the narrow portion is in communication with the first region and the second region and has a cross-sectional area smaller than the first region and the second region,
   a cathode in the electrode system is arranged so as to be positioned on the upstream side of the narrow portion,
   an anode in the electrode system is arranged so as to be positioned on the downstream side of the narrow portion, and
   movement of air bubbles generated in the narrow portion toward the upstream side of the narrow portion is prevented, wherein the upper surface of the first region has a concave portion configured to hold the air bubbles with the result of preventing movement of the air bubbles.

6. The plasma spectrometry method according to claim 5, wherein the movement of the air bubbles is prevented in the first region.

7. The plasma spectrometry method according to claim 5, wherein the cross section of the first region contains a cross-sectional area configured to prevent movement of air bubbles generated in the narrow portion from the narrow portion toward the upstream side of the first region.

8. The plasma spectrometry method according to claim 7, wherein the upper surface of the first region is arranged at a height which inhibits movement of air bubbles generated in the narrow portion from the narrow portion toward the upstream side of the first region, from the bottom surface of the first region.

9. The plasma spectrometry method according to claim 7, wherein:
   the upper surface of the first region has a tapered portion and a parallel portion,
   the tapered portion is enlarged in the height direction from the end on the upstream side of the narrow portion toward the upstream side of the first region relative to the bottom surface of the first region, and
   the parallel portion is parallel with the bottom surface of the first region from the end on the upstream side of the tapered portion toward the upstream side of the first portion.

* * * * *